United States Patent
Maeda et al.

(10) Patent No.: US 10,085,627 B2
(45) Date of Patent: Oct. 2, 2018

(54) IMAGE PICKUP APPARATUS AND ENDOSCOPE

(71) Applicant: OLYMPUS CORPORATION, Tokyo (JP)

(72) Inventors: Kazuya Maeda, Nagano (JP); Shoichiro Kawayoke, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/652,908

(22) Filed: Jul. 18, 2017

(65) Prior Publication Data
US 2017/0311786 A1    Nov. 2, 2017

Related U.S. Application Data

(63) Continuation of application No. PCT/JP2015/051884, filed on Jan. 23, 2015.

(51) Int. Cl.
*H04N 5/225* (2006.01)
*A61B 1/05* (2006.01)
(Continued)

(52) U.S. Cl.
CPC .............. *A61B 1/051* (2013.01); *A61B 1/005* (2013.01); *A61B 1/0011* (2013.01);
(Continued)

(58) Field of Classification Search
CPC . A61B 1/051; A61B 1/00114; A61B 1/00124; A61B 1/0011; A61B 1/005; H01L 27/14632; H01L 27/14636; H01L 24/16; H01L 27/14618; H01L 27/14687; H01L 2224/16227; H04N 5/2256; H04N 2005/2255
See application file for complete search history.

(56) References Cited

U.S. PATENT DOCUMENTS 7,745,259 B2 * 6/2010 Sasaki ................. H01L 21/6835
257/781
8,450,852 B2 * 5/2013 Kondo ................. H01L 21/4857
257/701
(Continued)

FOREIGN PATENT DOCUMENTS

JP    H07-283364 A    10/1995
JP    2008-118568 A    5/2008
(Continued)

OTHER PUBLICATIONS

International Search Report dated Apr. 21, 2015 issued in PCT/JP2015/051884.

*Primary Examiner* — Hung Lam
(74) *Attorney, Agent, or Firm* — Scully, Scott, Murphy & Presser, P.C.

(57) ABSTRACT

An image pickup apparatus includes an image pickup device configured such that a plurality of electrode pads are disposed in a row on an inclined surface; a wiring board configured such that a plurality of first bonded electrodes that are bonded to the plurality of electrode pads via first solder bumps, respectively, are disposed in a row on a first end portion, and a plurality of second bonded electrodes are disposed in a row on a second end portion; and a signal cable configured to be bonded to the plurality of second bonded electrodes via second solder bumps, respectively. The wiring board includes a first protective film which covers the first end portion, and a second protective film which covers the second end portion, and is of a thickness that is greater than a thickness of the first protective film and less than a height of the second solder bumps.

10 Claims, 8 Drawing Sheets

(51) Int. Cl.
*A61B 1/00* (2006.01)
*A61B 1/005* (2006.01)
*H01L 27/146* (2006.01)
*H01L 23/00* (2006.01)

(52) U.S. Cl.
CPC ...... *A61B 1/00114* (2013.01); *A61B 1/00124* (2013.01); *H01L 24/16* (2013.01); *H01L 27/14618* (2013.01); *H01L 27/14632* (2013.01); *H01L 27/14636* (2013.01); *H01L 27/14687* (2013.01); *H04N 5/2256* (2013.01); *H01L 2224/16227* (2013.01); *H04N 2005/2255* (2013.01)

(56) References Cited

U.S. PATENT DOCUMENTS

| | | | | |
|---|---|---|---|---|
| 2008/0061437 | A1* | 3/2008 | Kohara | H01L 23/13 257/738 |
| 2016/0133484 | A1* | 5/2016 | Akiba | H01L 21/4853 438/613 |
| 2017/0033142 | A1* | 2/2017 | Kobayashi | H01L 27/14618 |
| 2018/0040652 | A1* | 2/2018 | Maeda | H01L 27/14618 |

FOREIGN PATENT DOCUMENTS

| | | |
|---|---|---|
| JP | 2009-016623 A | 1/2009 |
| JP | 2009-295825 A | 12/2009 |
| JP | 2013-103011 A | 5/2013 |
| JP | 2014-075764 A | 4/2014 |
| WO | WO 2014/054419 A1 | 4/2014 |

\* cited by examiner

IMAGE PICKUP APPARATUS AND ENDOSCOPE

CROSS REFERENCE TO RELATED APPLICATION

This application is a continuation application of PCT/JP2015/051884 filed on Jan. 23, 2015, the entire contents of which are incorporated herein by this reference.

BACKGROUND OF THE INVENTION

1. Field of the Invention

The present invention relates to an image pickup apparatus equipped with an image pickup device in which a plurality of electrode pads are disposed in a row on an inclined surface that is sharply inclined with respect to a light receiving surface, and a wiring board in which a plurality of first bonded electrodes that are bonded to the plurality of electrode pads of the image pickup device via solder bumps, respectively, are disposed in a row on an end portion. The present invention also relates to an endoscope equipped with the image pickup apparatus.

2. Description of the Related Art

Image pickup apparatuses manufactured by wafer level CSP technology are small, and thus greatly contribute to reducing a diameter of an endoscope.

In a manufacturing method of a wafer level CSP type image pickup apparatus, first, a plurality of light receiving portions, and a plurality of external electrodes connected to the light receiving portions, respectively, are formed on a semiconductor wafer. A glass wafer is then adhered to a light receiving surface of the semiconductor wafer, such that a bonded wafer is fabricated. A via reaching the external electrodes from a facing surface side that faces the light receiving surface of the bonded wafer is formed. The light receiving surface of the image pickup apparatus obtained by cutting the bonded wafer is covered by a cover glass, but an electrical signal is able to be transmitted to/received from the light receiving portion via the external electrodes that are exposed on a bottom surface of the via.

Japanese Patent Application Laid-Open Publication No. 2014-75764 disclosed an image pickup device in which a plurality of electrode pads that are connected to external electrodes, respectively, on a light receiving surface are disposed in a row on an inclined wall surface of a through-trench. The plurality of electrode pads are connected, via bumps, to a plurality of bonded electrodes, respectively, that are disposed in a row on an end portion of a wiring board. Signal cables are bonded to the other end portion of the wiring board.

An arrangement interval (arrangement pitch) of electrode pads of a small image pickup apparatus is extremely narrow. Therefore, when solder bonding the electrode pads of the image pickup device and the bonded electrodes of the wiring board, the molten solder may spread out and adjacent bumps may short circuit, if the solder bumps are large. Therefore, it is necessary to arrange small (short) solder bumps according to the arrangement pitch. On the other hand, the wiring board and the signal cables must be bonded via large solder bumps in order to ensure bond reliability.

That is, achieving bond reliability with both the bonds of the signal cables and the bonds of the image pickup device is not easy because the sizes of suitable solder bumps are different for the bonds of the signal cables and the bonds of the image pickup device.

Note that Japanese Patent Application Laid-Open Publication No. 2009-016623 describes an image pickup apparatus in which a plurality of external electrodes are exposed on a bottom surface of a groove, by forming a groove (a wide via) that reaches a light receiving surface from a facing surface side.

SUMMARY OF THE INVENTION

An image pickup apparatus according to an embodiment of the present invention is an image pickup apparatus that includes an image pickup device configured such that a light receiving portion is formed on a light receiving surface, and a plurality of electrode pads that are connected to the light receiving portion are disposed in a row on an inclined surface that is inclined with respect to the light receiving surface; a transparent member configured to be adhered via an adhesive layer so as to cover the light receiving surface; a wiring board configured such that a plurality of first bonded electrodes that are bonded to the plurality of electrode pads of the image pickup device via a plurality of first solder bumps, respectively, are disposed in a row on a first end portion of a first main surface, and a plurality of second bonded electrodes are disposed in a row on a second end portion opposing the first end portion; and a signal cable configured to include a plurality of conducting wires that are bonded to the plurality of second bonded electrodes of the wiring board via a plurality of second solder bumps of a height higher than a height of the first solder bumps, respectively. The wiring board includes a first protective film which covers the first end portion of the first main surface, surrounds the plurality of first solder bumps, and is of a thickness that is less than the height of the first solder bumps, and a second protective film which covers the second end portion of the first main surface, surrounds the plurality of second solder bumps, and is of a thickness that is greater than the thickness of the first protective film and less than the height of the second solder bumps.

Also, an endoscope according to another embodiment includes, on a distal end portion of an insertion portion, an image pickup apparatus that includes an image pickup device configured such that a light receiving surface is formed on a light receiving surface, and a plurality of electrode pads that are connected to the light receiving portion are disposed in a row on an inclined surface that is inclined with respect to the light receiving surface; a transparent member configured to be adhered via an adhesive layer so as to cover the light receiving surface; a wiring board configured such that a plurality of first bonded electrodes that are bonded to the plurality of electrode pads of the image pickup device via a plurality of first solder bumps, respectively, are disposed in a row on a first end portion of a first main surface, and a plurality of second bonded electrodes are disposed in a row on a second end portion opposing the first end portion; and a signal cable configured to include a plurality of conducting wires that are bonded to the plurality of second bonded electrodes of the wiring board via a plurality of second solder bumps of a height higher than a height of the first solder bumps, respectively. The wiring board includes a first protective film which covers the first end portion of the first main surface, surrounds the plurality of first solder bumps, and is of a thickness that is less than the height of the first solder bumps, and a second protective film which covers the second end portion of the first main surface, surrounds the plurality of second solder bumps, and is of a thickness that is greater than the thickness of the first protective film and less than the height of the second solder bumps.

DETAILED DESCRIPTION OF THE PREFERRED EMBODIMENTS

Figure 1:
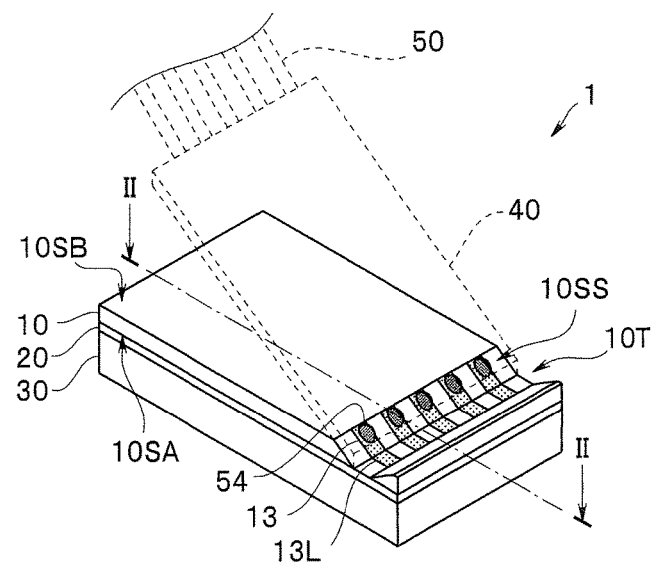
FIG. 1 is a perspective view schematically showing a configuration of an image pickup apparatus according to a first embodiment.

Hereinafter, embodiments of the present invention will be described with reference to the drawings. Note that the drawings are representative, and the relationship between thickness and width of respective members, proportion of thickness of each member, the number of electrode pads, and arrayed pits and the like are different in reality. Also, the drawings also include portions in which the relationships and proportions of the dimensions are different even among drawings. Furthermore, some of the components, for example, a silicon oxide layer of a surface of a silicon substrate and wires and the like, are not shown in the drawings.

Figure 2:
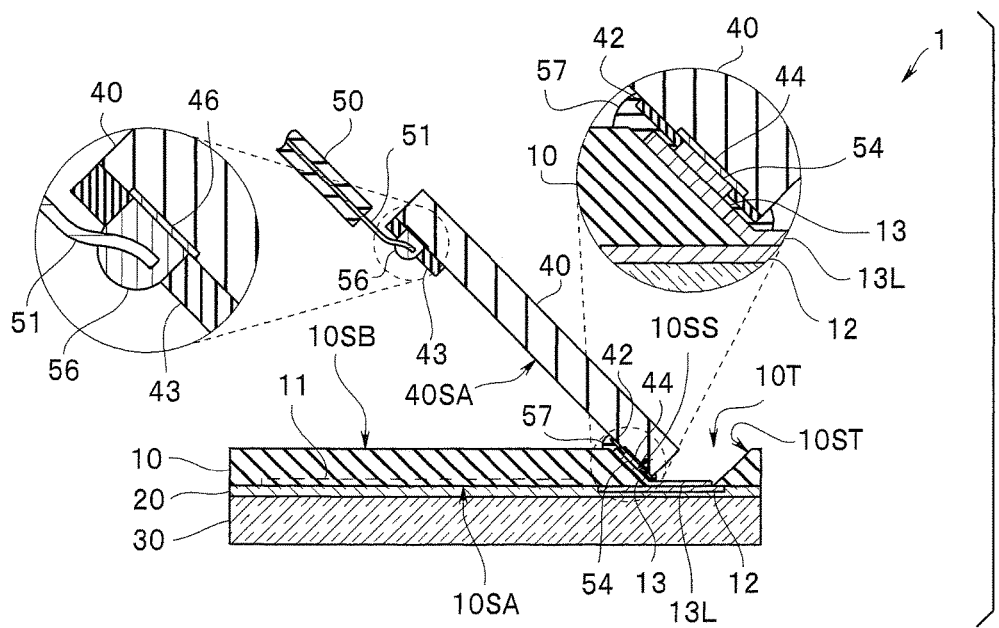
FIG. 2 is a sectional view taken along line II-II in FIG. 1.
Figure 3:
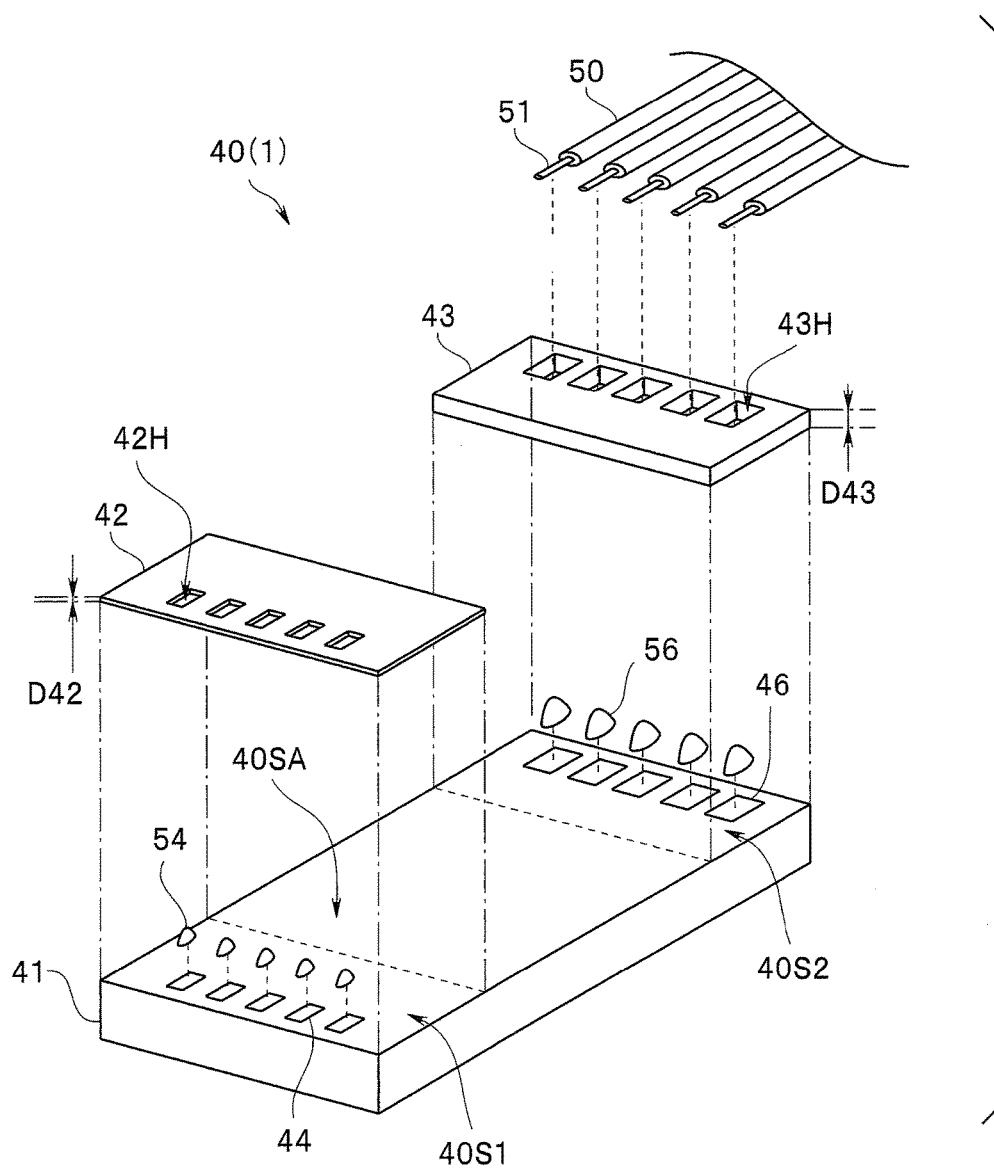
FIG. 3 is an exploded perspective view of a wiring board of the image pickup apparatus according to the first embodiment.

As shown in FIG. 1 to FIG. 3, an image pickup apparatus 1 includes an image pickup device 10 formed from a silicon substrate, a wiring board 40, and a signal cable 50. A plurality of external electrodes 12 that are electrically connected via a light receiving portion 11 and wires (not shown), are disposed in a row on an end portion of a light receiving surface 10SA on which the light receiving portion 11 of the image pickup device 10 that has a generally rectangular shape is formed.

The entire surface of the light receiving surface 10SA of the image pickup device 10 is covered by a cover glass 30 that is a transparent member, via an adhesive layer 20.

The image pickup device 10 has a groove 10T having, as wall surfaces, an inclined surface 10SS and an inclined surface 10ST that are both sharply inclined with respect to the light receiving surface 10SA, on a facing surface 10SB side of the image pickup device 10. Back surfaces of the external electrodes 12 are exposed on a bottom surface of the groove 10T. That is, the groove 10T is a wide via that passes through the silicon substrate.

Also, a plurality of electrode pads 13 that are electrically connected via the external electrodes 12 and wires 13L, respectively, are disposed in a row on the inclined surface 10SS. Therefore, the electrode pads 13 are electrically connected to the light receiving portion 11. Note that extending portions of the wires 13L may also be the electrode pads 13.

On the other hand, on a first main surface 40SA of a substrate 41 of a flat plate-shaped wiring board 40, a plurality of first bonded electrodes 44 are disposed in a row on a first end portion 40S1, and a plurality of second bonded electrodes 46 are disposed in a row on a second end portion 40S2 opposing the first end portion 40S1. The first bonded electrodes 44 are bonded to the electrode pads 13 via first solder bumps 54. On the other hand, the second bonded electrodes 46 are bonded to conducting wires 51 of signal cables 50 via second solder bumps 56. The first bonded electrodes 44 and the second bonded electrodes 46 are electrically connected via wires (not shown).

In order to increase the bond reliability, the bonding sites of the first bonded electrodes 44 and the electrode pads 13 are sealed with sealing resin 57.

An arrangement pitch of the first bonded electrodes 44 is narrower than an arrangement pitch of the second bonded electrodes 46. Also, a height H54 of the first solder bumps 54 is lower than a height H56 of the second solder bumps 56. For example, the first solder bumps 54 have a height H54 of 10 μm, while the second solder bumps 56 have a height H56 of 50 μm.

A first protective film 42 that surrounds the plurality of first solder bumps 54 is arranged on the first end portion 40S1 of the first main surface 40SA of the wiring board 40. On the other hand, a second protective film 43 that surrounds the plurality of second solder bumps 56 is arranged on the second end portion 40S2 opposing the first end portion 40S1. That is, a plurality of openings 42H exist in the first protective film 42, and a plurality of openings 43H exist in the second protective film 43.

A thickness D43 of the second protective film 43 is thicker than a thickness D42 of the first protective film 42. For example, the first protective film 42 has a thickness D42 of 1.0 μm, while the second protective film 43 has a thickness D43 of 30 μm.

With the image pickup apparatus 1, the height H54 of the first solder bumps 54 greatly differs from the height H56 of the second solder bumps 56. However, the first solder bumps 54 and the second solder bumps 56 are surrounded by the first protective film 42 and the second protective film 43 that have thicknesses according to the respective heights of the first solder bumps 54 and the second solder bumps 56. Therefore, even when the solder melts, the solder will not spread around, and both are able to be reliably bonded. That is, the reliability of the bonded sites is high with the image pickup apparatus 1.

<Manufacturing Method>

Next, a manufacturing method of the image pickup apparatus 1 will be described. Note that the image pickup device 10 to which the cover glass 30 is adhered is fabricated by cutting a bonded wafer, but hereinafter will be described as an individual image pickup device.

Figure 4A:
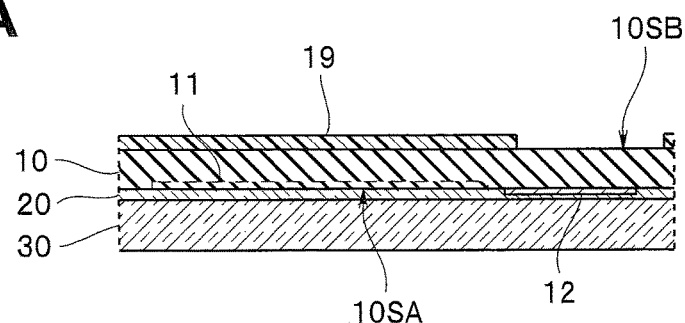
FIG. 4A is a sectional view illustrating a manufacturing method of an image pickup device of the image pickup apparatus according to the first embodiment.

As shown in FIG. 4A, the light receiving portion 11 and the plurality of external electrodes 12 that are connected to the light receiving portion 11 by wires (not shown), are formed using well-known semiconductor manufacturing technology, on the light receiving surface 10SA of a silicon substrate (image pickup device) 10. Each of the external electrodes 12 is made of a metal conductor such as copper or aluminum. The cover glass 30 (glass wafer) is adhered to the light receiving surface 10SA via the adhesive layer 20. The adhesive layer 20 is made of a transparent ultraviolet curable resin, for example. Also, an etching mask 19 formed by a photoresist, for example, is arranged on the facing surface 10SB that faces the light receiving surface 10SA of the silicon substrate 10. The etching mask 19 has generally rectangular openings in an etching region, i.e., directly above the external electrodes 12.

Figure 4B:
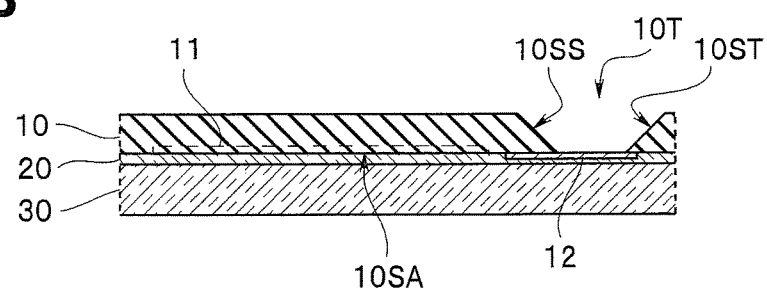
FIG. 4B is a sectional view illustrating a manufacturing method of the image pickup device of the image pickup apparatus according to the first embodiment.

As shown in FIG. 4B, the silicon substrate 10 is subjected to wet etching processing using an alkaline solution such as KOH or TMAH from the facing surface 10SB side to form the groove 10T. The groove 10T is a wide via that passes through the silicon substrate 10.

Wall surfaces of the groove 10T formed by anisotropic etching become the inclined surfaces 10SS and 10ST that are sharply inclined with respect to the light receiving surface 10SA. Also, back surfaces of the plurality of external electrodes 12 are exposed on a bottom surface of the groove 10T. Note that the applicant discloses the manufacturing method of the groove 10T and the like in detail in Japanese Patent Application Laid-Open Publication No. 2009-016623.

Figure 4C:
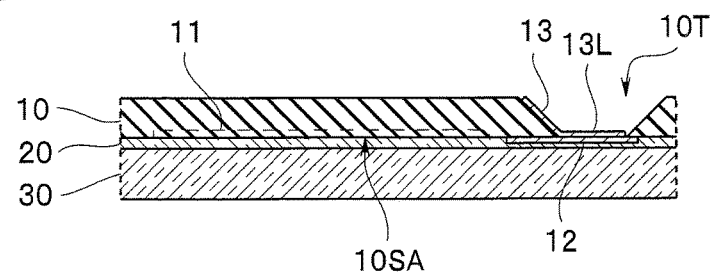
FIG. 4C is a sectional view illustrating a manufacturing method of the image pickup device of the image pickup apparatus according to the first embodiment.

As shown in FIG. 4C, the electrode pads 13 are arranged on the inclined surface 10SS. The electrode pads 13 are electrically connected to the external electrodes 12 by the wires 13L that extend from the bottom surface of the groove 10T to the inclined surface 10SS.

Figure 5:
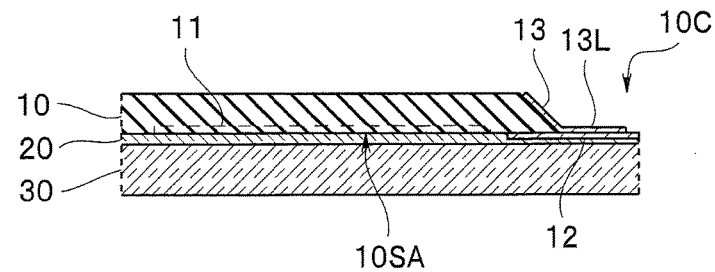
FIG. 5 is a sectional view illustrating a manufacturing method of an image pickup device of an image pickup apparatus according to a modification of the first embodiment.

Note that a cutaway portion 10C may also be formed instead of the groove 10T, as shown in FIG. 5. The cutaway portion 10C may be formed by dry etching, physical etching or mechanical grinding or the like. An image pickup apparatus according to a modification that includes an image pickup device with the cutaway portion 10C has a smaller diameter than the image pickup apparatus 1.

On the other hand, the wiring board 40 is a flexible wiring board having polyimide as the substrate 41, for example, as shown in FIG. 3. A non-flexible substrate made of glass epoxy resin or the like may also be used as the substrate 41. However, a flexible substrate is preferable in order to accommodate the substrate in a projection plane of the image pickup device 10, as will be described later.

The thickness of the first protective film 42 is preferably a thickness according to the arrangement pitch of the first bonded electrodes 44 of the small image pickup apparatus 1, in other words, the height H54 of the first solder bumps 54, for example, between 0.1 μm and 3.0 μm, inclusive. Even with a thin film thickness within this range, the first protective film 42 is preferably made of solder repellent material in order to prevent a short circuit between adjacent first solder bumps 54. Solder repellent material is so-called "solder-repelling" material having poor solder wettability, and of course is material having a higher upper temperature limit than a solder bonding temperature.

Solder repellent material in which a contact angle θ with respect to the solder is equal to or greater than 45 degrees, and preferably, equal to or greater than 60 degrees, may be used for the first protective film 42. If the contact angle θ with respect to the solder of the first protective film 42 is equal to or greater than this range, the solder is able to be prevented from spreading out. The larger the contact angle θ is the better, so the upper limit may be 180 degrees.

As the solder repellent material, silicon oxide, magnesium fluoride, aluminum nitride, boron nitride, silicon nitride, silicon carbide, boron carbide, calcium carbide, diamond like carbon (DLC), polytetrafluoroethylene (PTFE), or tetrafluoroethylene-perfluoroalkyl vinyl ether copolymer (PFA) or the like may be used.

As the solder repellent material, silicon oxide or silicon nitride, which is easy to form as a film and pattern, is preferably used. The solder repellent material is formed as a film by a sputtering method, a vapor deposition method, or a CVD method. Note that after being arranged on the entire surface of the first main surface 40SA, for example, the first protective film 42 is removed by etching or the like at the openings 42H of the first protective film 42 and in the region other than the first end portion 40S1.

Note that the solder wettability can be evaluated by melting 20 mg of solder on a test surface, and measuring the contact angle θ of the melted solder with respect to the test surface. The contact angle θ of a bonded member 23 with respect to polyimide that is the substrate 41 of the wiring board is less than 30 degrees, while the contact angle θ with respect to silicon oxide is equal to or greater than 70 degrees.

On the other hand, the thickness of the second protective film 43 is preferably between 5 μm and 100 μm, inclusive, for example, according to the height H56 of the second solder bumps 56. For the second protective film 43 of a thickness in this range, a solder resist made of an epoxy resin or the like is preferably arranged by a printing method or an inkjet method or the like. Note that the second protective film 43 made of resin has excellent flexibility, so even if the second protective film 43 is thick, the flexibility of the wiring board 40 will not be impaired.

If the second protective film 43 is arranged by a printing method, the openings 43H of the second protective film 43 are taken into account when designing a printing screen.

The first solder bumps 54 and the second solder bumps 56 are arranged on the wiring board 40. The first solder bumps 54 and the second solder bumps 56 are made of lead-free solder such as a SnAgCu alloy or a SnZnAl alloy, and the composition of both may be the same or different. For example, the first and second solder bumps 54 and 56 may be arranged by printing solder paste onto the bonded electrodes 44 and 46, or by a plating method. Note that the first solder bumps 54 may be arranged on the electrode pads 13 of the image pickup device 10.

As shown in FIG. 2 and the like, the first bonded electrodes 44 of the wiring board 40 and the electrode pads 13 of the image pickup device 10 are bonded via the first solder bumps 54. That is, the first end portion 40S1 of the wiring board 40 is fixed at an angle sharply inclined, similar to the inclined surface 10SS of the image pickup device 10, with respect to the light receiving surface 10SA of the image pickup device 10. The first solder bumps 54 are surrounded by the first protective film 42 of a thickness according to the height H54. Therefore, even if the first solder bumps 54 melt, the solder will not spread around, and the first bonded electrodes 44 of the wiring board 40 and the electrode pads 13 of the image pickup device 10 will bond.

The sealing resin 57 is filled into the bonding sites and hardened. The sealing resin 57 is, for example, a thermosetting epoxy resin that is liquid in an unhardened state.

Next, the conducting wires 51 of the signal cables 50 are bonded to the second bonded electrodes 46 of the wiring board 40 via the second solder bumps 56. The second solder bumps 56 are surrounded by the second protective film 43 of a height according to the height H56. Therefore, even if the second solder bumps 56 melt, the solder will not spread around, and the second bonded electrodes 46 of the wiring board 40 and the conducting wires 51 of the signal cables 50 will bond.

Note that the wiring board 40 to which the signal cables 50 are bonded may also be bonded to the image pickup device 10. Also, the image pickup device 10, the wiring board 40 and the signal cables 50 that are temporarily fixed may be simultaneously bonded by reflow processing.

As described above, with the image pickup apparatus 1, the reliability of the bonding sites is high. In particular, the first protective film 42 is extremely thin compared to the second protective film 43 formed by a solder resist, but because the first protective film 42 is made of solder repellent material, a short circuit will not occur due to melted solder spreading around.

Note that with the image pickup apparatus 1, when viewing the image pickup device 10 from the thickness direction in a plan view, the wiring board 40 positioned on the rear side (the side opposite the cover glass) with respect to the image pickup device 10, is positioned entirely within a region that overlaps with the image pickup device 10, i.e., within the projection plane of the image pickup device 10. In particular, when the wiring board 40 is flexible, even if the length of the wiring board 40 is long, the wiring board 40 can be entirely disposed within the projection plane of the image pickup device 10 by being bent and deformed. The image pickup apparatus 1 has a small diameter because the wiring board 40 does not protrude out beyond the outer shape of the image pickup device 10.

Second Embodiment

Next, an image pickup apparatus 1A according to a second embodiment and an image pickup apparatus 1B according to a modification of the second embodiment will be described. Note that because the image pickup apparatuses 1A and 1B are similar to the image pickup apparatus 1, constituent elements having the same function will be denoted by like reference numerals and descriptions of these constituent elements will be omitted.

Figure 6:
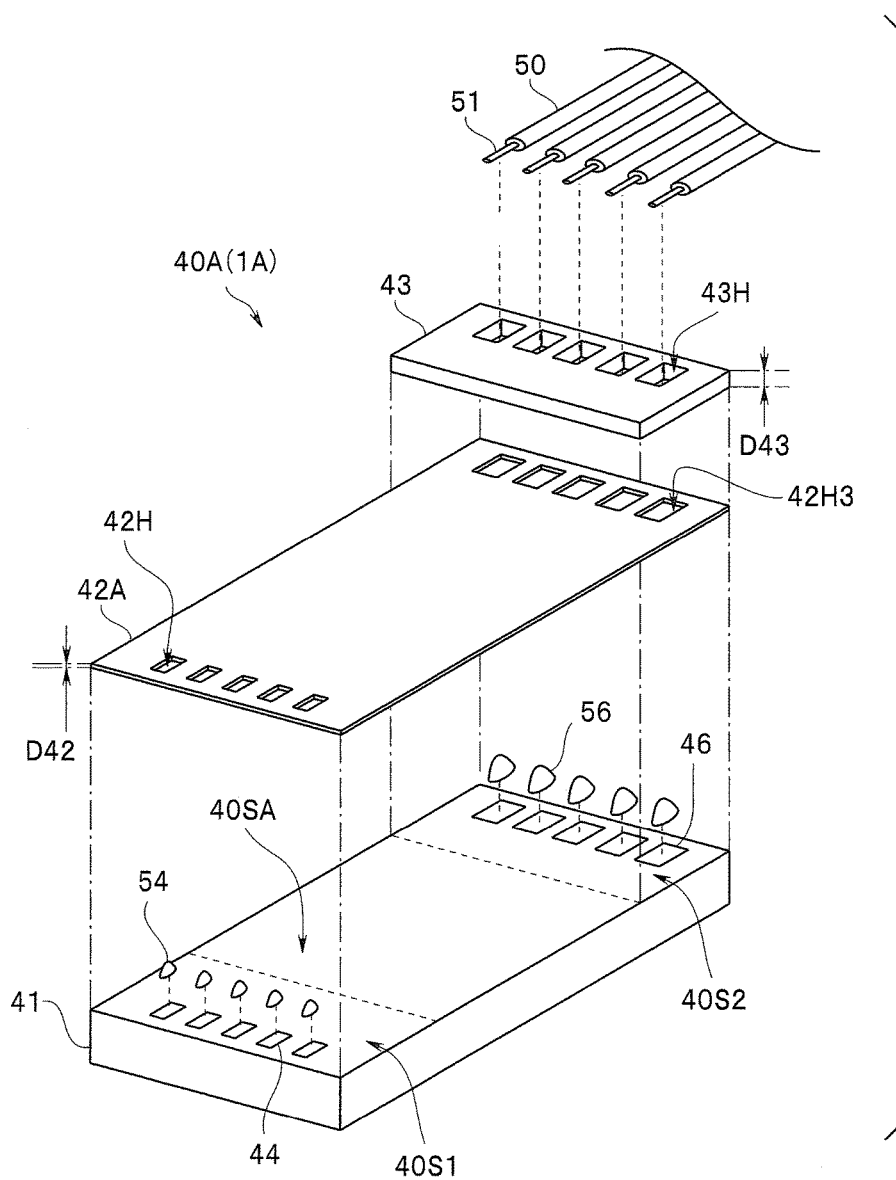
FIG. 6 is an exploded perspective view of a wiring board of an image pickup apparatus according to a second embodiment.

As shown in FIG. 6, with the image pickup apparatus 1A, a first protective film 42A covers not just the first end portion 40S1 of the first main surface 40SA of the wiring board 40, but the entire first main surface 40SA of the wiring board 40. The first protective film 42A has not only openings 42H corresponding to the first solder bumps 54, but also openings 42H3 corresponding to the second solder bumps 56. That is, the first protective film 42A surrounds the first solder bumps 54 and the second solder bumps 56.

With the image pickup apparatus 1A, the second solder bumps 56 is bonded to the conducting wires 51 via not only the openings 43H in the second protective film 43, but also the openings 42H3 in the first protective film 42A.

Figure 7:
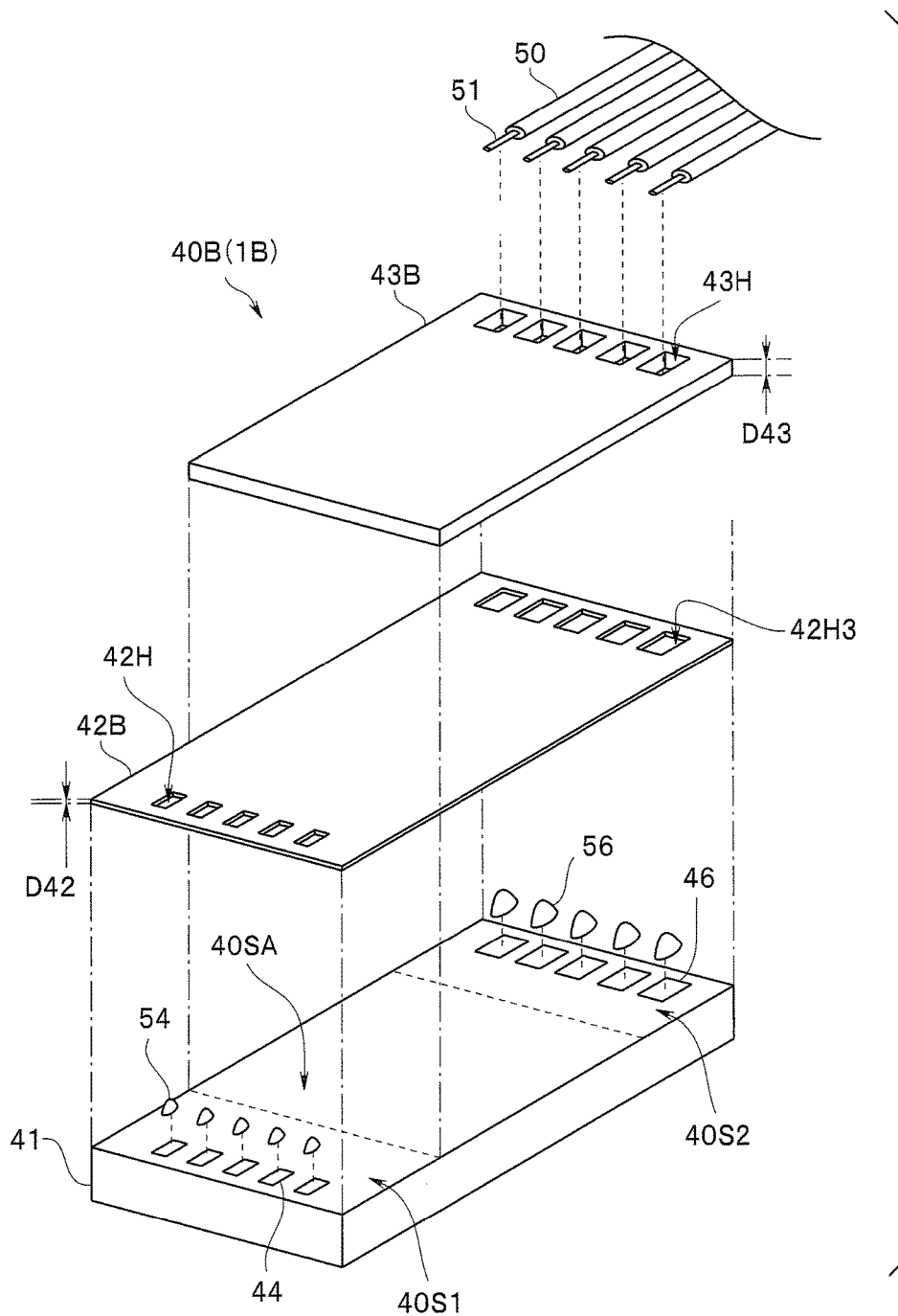
FIG. 7 is an exploded perspective view of a wiring board of an image pickup apparatus according to a modification of the second embodiment.

On the other hand, as shown in FIG. 7, with the image pickup apparatus 1B according to the modification, a first protective film 42B covers not only the first end portion 40S1 of the first main surface 40SA of the wiring board 40, but the entire first main surface 40SA of the wiring board 40.

On the other hand, a second protective film 43B covers the region excluding the first end portion 40S1 of the first main surface 40SA of the wiring board 40.

The image pickup apparatus 1A and the image pickup apparatus 1B have the effects of the image pickup apparatus 1. Furthermore, with the image pickup apparatus 1A, the second solder bumps 56 are also surrounded by the first protective film 42A, so the reliability is higher than the reliability with the image pickup apparatus 1.

Also, with the image pickup apparatus 1B, the first protective film 42A is covered by the second protective film 43B except at the first end portion 40S1, so even if the wiring board 40 greatly deforms, the first protective film 42A that tends to crack and the like easily is covered by the flexible thick second protective film 43B, so the reliability is even higher than the reliability with the image pickup apparatus 1A.

Third Embodiment

Next, an image pickup apparatus 1C according to a third embodiment will be described. Note that the image pickup apparatus 1C is similar to the image pickup apparatuses 1, 1A, and 1B, and has similar effects, so constituent elements having the same function will be denoted by like reference numerals and descriptions of these constituent elements will be omitted.

Figure 8:
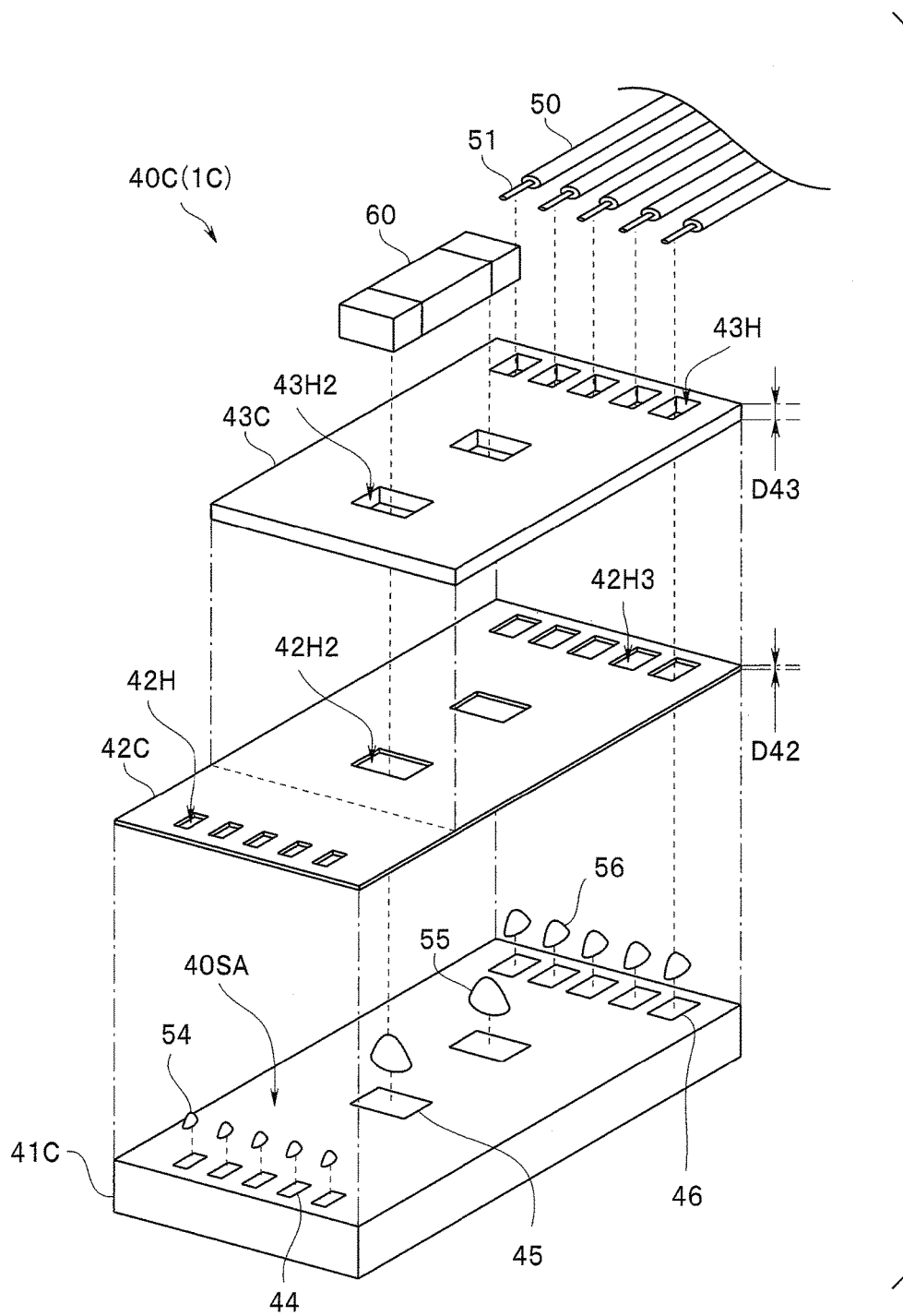
FIG. 8 is an exploded perspective view of a wiring board of an image pickup apparatus according to a third embodiment.
Figure 9:
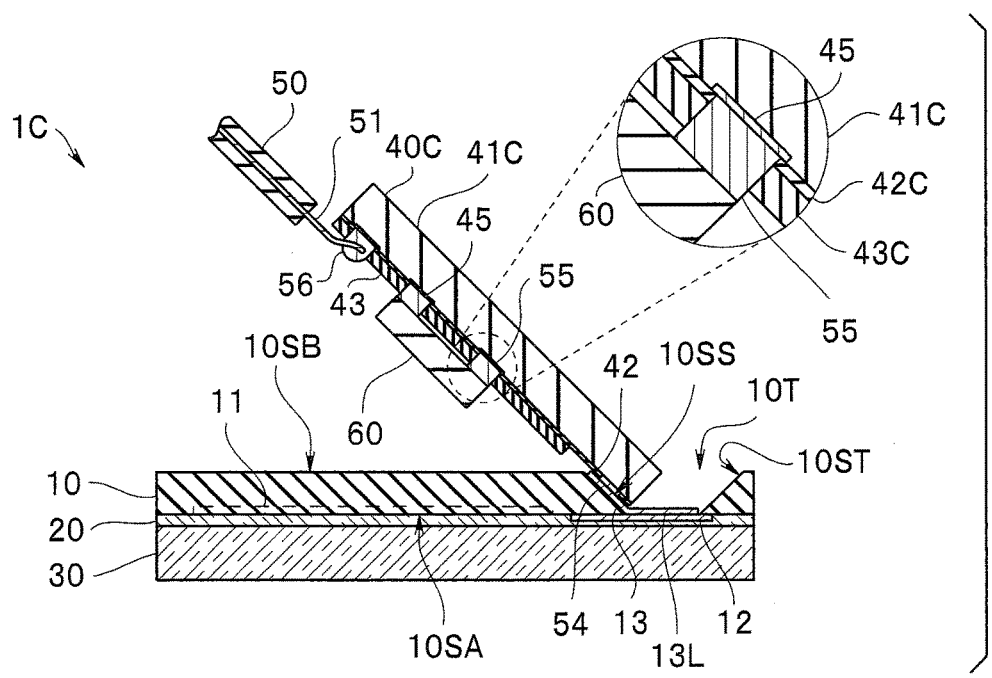
FIG. 9 is a sectional view of the image pickup apparatus according to the third embodiment.

As shown in FIG. 8 and FIG. 9, an electronic component 60 is mounted on the first main surface 40SA of a wiring board 40C of the image pickup apparatus 1C. That is, a plurality of third bonded electrodes 45 are arranged on the first main surface 40SA of the wiring board 40C. The electronic component 60 is bonded to the plurality of third bonded electrodes 45 via a plurality of third solder bumps 55, respectively. Also, the first protective film 42C and the second protective film 43C are surrounding the plurality of third solder bumps 55, i.e., openings 42H2 exist in the first protective film 42C, and openings 43H2 exist in the second protective film 43C.

The positions of the third bonded electrodes 45 are designed according to the positions of the bonded portions of the electronic component 60, which is a chip condenser or a chip inductor or the like. Also, the number of bonded portions of the electronic component 60 may also be three or more. Furthermore, only one electronic component 60 is mounted to the wiring board 40C, but a plurality of electronic components 60 may also be mounted to the wiring board 40C. Also, the electronic component 60 may also be mounted to a second main surface 20SB.

The image pickup apparatus 1C has a small diameter because the wiring board 40C to which the electronic component 60 is mounted does not protrude out beyond the outer shape of the image pickup device 10.

Fourth Embodiment

Next, an endoscope 2 according to a fourth embodiment will be described. Note that the endoscope 2 is equipped with one of the image pickup apparatuses 1, 1A to 1C already described, on a distal end portion 3A of an insertion portion 3. Therefore, a description of the image pickup apparatus 1 and the like will be omitted.

Figure 10:
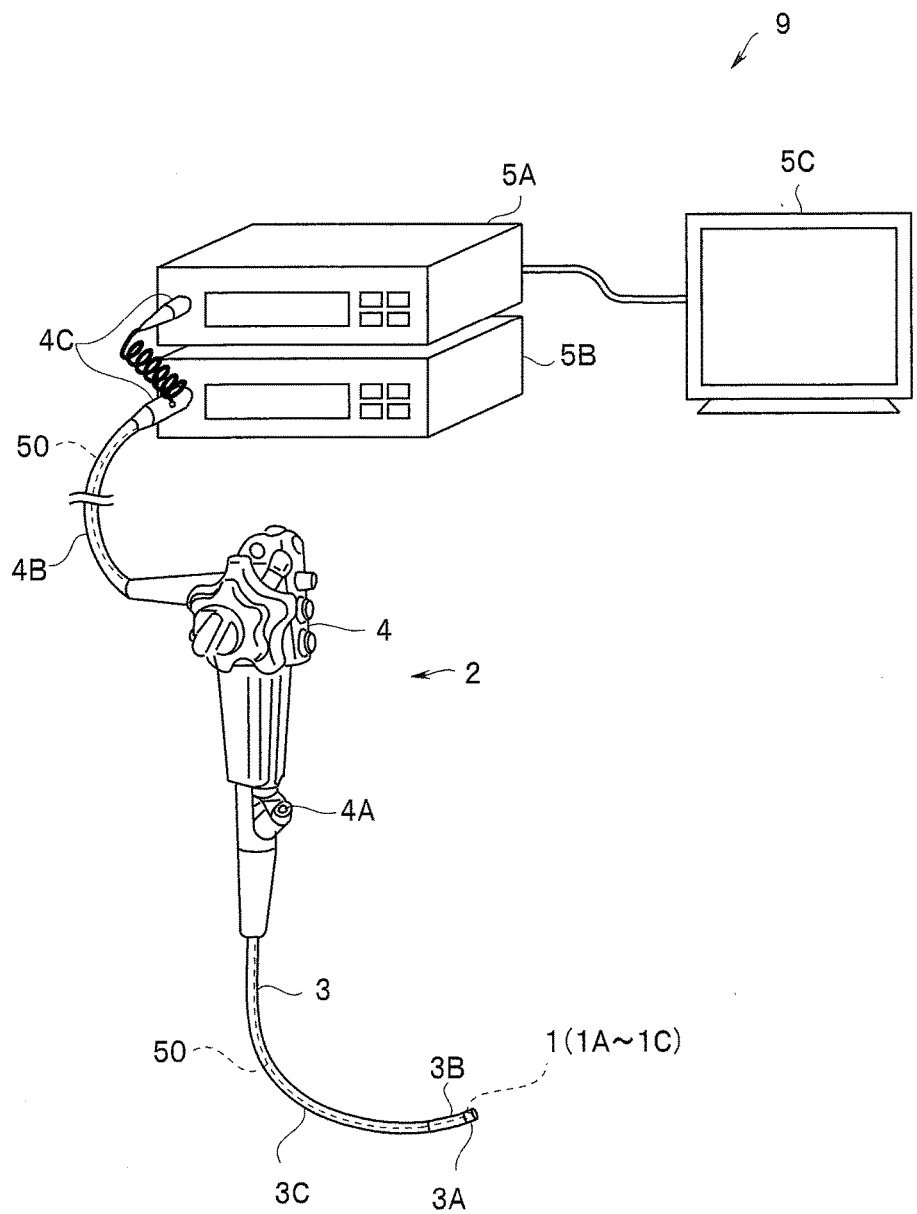
FIG. 10 is a perspective view of an endoscope system including an endoscope according to the third embodiment.

As shown in FIG. 10, an endoscope system 9 that includes the endoscope 2 is equipped with the endoscope 2, a processor 5A, a light source apparatus 5B, and a monitor 5C. The endoscope 2 picks up an in-vivo image of a subject by the insertion portion 3 being inserted into a body cavity of the subject, and outputs an image pickup signal. That is, the endoscope 2 is equipped with one of the image pickup apparatuses 1, 1A to 1C on the distal end portion of the insertion portion 3.

An operation portion 4 provided with various kinds of buttons that operate the endoscope 2 is arranged on a proximal end side of the insertion portion 3 of the endoscope 2. The operation portion 4 has a treatment instrument insertion opening 4A of a channel through which a treatment instrument such as biological forceps, an electric scalpel, and an examination probe or the like is inserted into a body cavity of the subject.

The insertion portion 3 is configured by the distal end portion 3A on which the image pickup apparatus 1 is arranged, a bendable bending portion 3B that is continuously connected to a proximal end side of the distal end portion 3A, and a flexible tube portion 3C that is continuously connected to a proximal end side of the bending portion 3B. The bending portion 3B bends in response to operation of the operation portion 4.

The signal cable 50 that is connected to the image pickup apparatus 1 of the distal end portion 3A is inserted through a universal cord 4B arranged on a proximal end portion side of the operation portion 4.

The universal cord 4B is connected to the processor 5A and the light source apparatus 5B via connectors 4C. The processor 5A controls the entire endoscope system 9, and performs signal processing on the image pickup signal output by the image pickup apparatus 1 and outputs the processed image pickup signal as an image signal. The monitor 5C displays the image signal output by the processor 5A.

The light source apparatus 5B is a white LED, for example. White light emitted by the light source apparatus 5B is guided to an illumination optical system 3D (see FIG. 2B) of the distal end portion 3A via a light guide (not shown) inserted through the universal cord 4B, and illuminates an object.

The endoscope 2 is highly reliable because the endoscope 2 is equipped with one of the highly reliable image pickup apparatuses 1, 1A to 1C on the distal end portion 3A of the insertion portion 3.

The present invention is not limited to the embodiments or modifications and the like described above. Various changes, modifications, and combinations and the like are possible without departing from the scope of the present invention.

What is claimed is:

1. An image pickup apparatus comprising:
    an image pickup device configured such that a light receiving portion is formed on a light receiving surface, and a plurality of electrode pads that are connected to the light receiving portion are disposed in a row on an inclined surface that is inclined with respect to the light receiving surface;
    a transparent member configured to be adhered via an adhesive layer so as to cover the light receiving surface;
    a wiring board configured such that a plurality of first bonded electrodes that are bonded to the plurality of electrode pads of the image pickup device via a plurality of first solder bumps, respectively, are disposed in a row on a first end portion of a first main surface, and a plurality of second bonded electrodes are disposed in a row on a second end portion opposing the first end portion; and
    a signal cable configured to include a plurality of conducting wires that are bonded to the plurality of second bonded electrodes of the wiring board via a plurality of second solder bumps of a height higher than a height of the first solder bumps, respectively, wherein
    the wiring board includes a first protective film which covers the first end portion of the first main surface, surrounds the plurality of first solder bumps, and is of a thickness that is less than the height of the first solder bumps, and a second protective film which covers the second end portion of the first main surface, surrounds the plurality of second solder bumps, and is of a thickness that is greater than the thickness of the first protective film and less than the height of the second solder bumps.

2. The image pickup apparatus according to claim 1, wherein:
    the first protective film is made of solder repellent material; and
    the second protective film is formed by a solder resist.

3. The image pickup apparatus according to claim 2, wherein the first protective film is made of silicon oxide or silicon nitride.

4. The image pickup apparatus according to claim 3, wherein:
    the first protective film is formed by a sputtering method, a vapor deposition method, or a CVD method; and
    the second protective film is formed by a printing method.

5. The image pickup apparatus according to claim 4, wherein the thickness of the first protective film is between 0.1 µm and 3 µm, inclusive.

6. The image pickup apparatus according to claim 4, wherein the first protective film covers the first main surface, and surrounds the plurality of second bonded electrodes.

7. The image pickup apparatus according to claim 6, wherein the wiring board is flexible.

8. The image pickup apparatus according to claim 7, wherein bond portions of the plurality of electrode pads and the plurality of first bonded electrodes are sealed by a sealing resin.

9. The image pickup apparatus according to claim 8, wherein:
    a plurality of third bonded electrodes are arranged on the first main surface of the wiring board;
    the first protective film and the second protective film surround the plurality of third bonded electrodes; and
    an electronic component is bonded to the plurality of third bonded electrodes via a plurality of third solder bumps, respectively.

10. An endoscope comprising the image pickup apparatus according to claim 1.

* * * * *